United States Patent [19]
Lee

[11] Patent Number: 5,976,167
[45] Date of Patent: Nov. 2, 1999

[54] INTRAMUSCULAR STIMULATOR HAVING A PUNCTURE AID

[76] Inventor: Young H. Lee, 114 Apley Dr., Cherry Hill, N.J. 08003

[21] Appl. No.: 09/055,469

[22] Filed: Apr. 6, 1998

Related U.S. Application Data

[63] Continuation-in-part of application No. 08/641,516, May 1, 1996, Pat. No. 5,735,868.

[51] Int. Cl.$^6$ .................................................. A61B 17/34
[52] U.S. Cl. .......................................... 606/189; 606/169
[58] Field of Search ................................... 606/189, 181, 606/169, 167, 185; 128/898

[56] References Cited

U.S. PATENT DOCUMENTS

| | | |
|---|---|---|
| 3,938,526 | 2/1976 | Anderson et al. ...................... 606/189 |
| 4,662,363 | 5/1987 | Romano et al. ......................... 606/189 |
| 4,966,164 | 10/1990 | Colsen et al. ............................ 606/189 |
| 5,211,175 | 5/1993 | Gleason et al. .......................... 606/189 |
| 5,676,684 | 10/1997 | Choi ........................................ 606/189 |

*Primary Examiner*—Michael Buiz
*Assistant Examiner*—Kevin Truong
*Attorney, Agent, or Firm*—Gary M. Cohen

[57] ABSTRACT

A motor driven needling device for treating patients having chronic muscular pain includes a motor driven poking tool for mounting a needle, a control unit for adjusting the frequency and the depth of the poking, a mechanical swivel arm for holding and positioning the tool, a remote switch for activating the motorized tool, and an aid useful in causing the needle to puncture the patient's skin once the tool is positioned at a proper location over the muscle to be treated.

15 Claims, 5 Drawing Sheets

INTRAMUSCULAR STIMULATOR HAVING A PUNCTURE AID

RELATED CASE

The present application is a continuation-in-part of prior U.S. patent application Ser. No. 08/641,516, filed May 1, 1996 now U.S. Pat. No. 5,735,868.

BACKGROUND OF THE INVENTION

The present invention generally relates to an apparatus for automating the treatment of muscular pain by intramuscular stimulation, and in particular, to improvement of the apparatus to facilitate the initial insertion of the needle in the affected muscles.

Intramuscular stimulation (IMS) is a known method used to treat muscular pain by inserting a needle into an affected muscle. Intramuscular stimulation was first developed, and initially described by Gunn, "Dry Needling of Muscle Motor Points for Chronic Low-Back Pain: A Randomized Clinical Trial With Long-Term Follow-up", Spine, Vol. 5, No. 3, pp. 279–291 (1980). The intramuscular stimulation method has also been used by others (see, e.g., Chu, "Dry Needling in Myofascial Pain Related to Lumbosacral Radiculopathy", European Journal of Physical Medicine and Rehabilitation, Vol. 5, No. 4, pp. 106–121 (1995). A detailed method for performing the intramuscular stimulation treatment is described in Gunn, *Treating Moyofascial Pain: Intramuscular Stimulation for Myofascial Pain Syndromes of Neuropathic Origin*, Health Sciences Center for Educational Resources, University of Washington, Seattle Wash. (ISBN: 1-55910-003-6).

Briefly, the method involves the insertion of a fine needle, similar to an acupuncture needle, into the involved muscle and stimulating the muscle by repeatedly moving the needle back and forth linearly within the muscle. In this disclosure, "back and forth" movement will be taken to mean that the needle is first pushed in a linear direction into the muscle, then partially withdrawn in a linear direction, and then pushed back in, again along the same linear path of penetration. This action is repeated many times, at each of several muscular sites. For brevity, such needle manipulation will be referred to as "poking" in the remainder of this disclosure.

The involved muscle is usually tightly contracted. Such tightness of the muscle tends to apply severe pressure or pinching forces to the nerve fibers within the muscle, thereby causing chronic pain. When the contracted muscle is made to relax by repeated intramuscular stimulation treatments, the pain eventually subsides. The frequency of the treatment depends on the severity of the muscle contraction. A severely contracted muscle will require more frequent treatments over longer periods, whereas the required frequency will be less for the more lightly injured muscles. Intramuscular stimulation treatment is most usually performed at multiple points to be most effective.

Although the method developed by Gunn, and used by others, is quite effective in treating patients with chronic muscular pain, it was found that in practice, the method itself was self-limiting because of its detrimental effects on the person administering the treatment. To treat a patient, it is necessary to manually poke a needle into the injured muscle at a rate of approximately one to two times per second. Usually, a treatment session lasts about 45 minutes. This results in a total number of manual poking steps on the order of 2,700 to 5,400 times per session. For the case of a person treating eight patients per day, each with a 45 minute treatment session, the total number of manual poking steps will be on the order of 21,600 to 43,200 times per day. This enormous number of repeated, manual poking steps could at times cause such severe strain and pain to the shoulder and neck muscles of the person performing the treatment that, in time, damage to that person's muscles could itself require treatment (frequently, by an intramuscular stimulation treatment).

Another factor to consider is that the manual poking of the needle was itself very painful to the patient. This is presumably because the needle is constantly accelerated and decelerated during manual insertion and withdrawal during the course of a treatment. For this reason, the patient usually had to be premedicated (e.g., with narcotics) to avoid the excessive discomfort occurring during the treatment.

To overcome the problems associated with conventional intramuscular stimulation treatment, U.S. patent application Ser. No. 08/641,516 discloses an automated, motor driven, needling instrument for administering an intramuscular stimulation treatment to patients suffering from chronic muscular pain. The disclosed apparatus replaces manually operated muscle stimulation with a muscle stimulator (a needle) which is mechanically linked to an electrically-driven motor, which is in turn electrically connected to a programmable control unit. In its preferred mode, the intramuscular needling device is mechanically linked to a linear action motor, allowing the motor to drive the needle continuously, back and forth within the muscle in a controlled manner. The person administering the treatment can then hold the instrument steadily at a desired treatment site while the motor provides controlled, uniform back and forth linear motion to the intramuscular stimulator needle, at fixed penetration depths. This was found to eliminate, to a great degree, the tedious muscle-straining labor involved in a conventional (manual) poking treatment, thereby relieving the physical burden on the person administering the treatment.

For extended intramuscular stimulation treatment sessions, a mechanical swivel arm is provided to hold the stimulator needling instrument, and a foot switch is provided to remotely turn the motor on and off. In this way, intramuscular stimulation treatments can be performed with minimal physical effort, helping to avoid muscle injury to the person administering the treatment.

A further, and major additional advantage resulting from the use of such a device is a dramatic reduction in the pain experienced by the patient during treatment. In a conventional, manual poking treatment, the needle is frequently accelerated and decelerated because of the uneven poking action which is inherent in a manual operation. This leads to a transient shearing action that is enormously painful to the patient. The constant speed and uniform motion provided by an automated poking apparatus has been found to eliminate such pain, to a very significant degree (e.g., clinical tests have shown about a 75% reduction in the pain experienced by the patient during treatment).

In practice, the automated intramuscular stimulation apparatus disclosed in U.S. patent application Ser. No. 08/641,516 has been found to work quite well in performing desired treatments. However, it has also been found that the apparatus can be still further improved to make the treatment process even more comfortable for the patient and more convenient for the person administering the treatment. For example, to begin intramuscular stimulation treatment, the needle must first puncture the skin. However, the skin is often very tough, and resistant to puncturing with even a very sharp needle, especially the skin found over the affected muscle. To minimize treatment pain, this puncturing step has to be performed as quickly as possible, and even so, the patient can experience significant discomfort.

It is therefore the principal object of the present invention to provide an automated intramuscular stimulation needling device which is not only capable of developing a mechanical, uniform back and forth motion for the stimulator needle, but which is further able to facilitate initial insertion of the needle to puncture the skin at the treatment site.

It is also an object of the present invention to provide an automated intramuscular stimulation needling device which is able to facilitate initial insertion of the needle to puncture the skin at the treatment site while minimizing the patient's discomfort during this portion of the procedure.

SUMMARY OF THE INVENTION

These and other objects which will become apparent are achieved in accordance with the present invention by providing an automated intramuscular stimulation needling device with a device which aids in the puncturing step, in association with the remaining automated functions of the needling device. Such a function is preferably implemented by mating a solenoid with the needle-receiving structures of the apparatus so that the initial puncturing step can be performed by the solenoid, responsive to an appropriate control signal.

For a further discussion of the puncturing aid of the present invention, reference is made to the detailed description which is provided below.

BRIEF DESCRIPTION OF THE DRAWINGS

It will be understood that the present invention may take form in various arrangements of parts, and that the following drawings are only for the purpose of illustrating a preferred embodiment of the invention and are not to be construed as limiting the scope of the invention.

DETAILED DESCRIPTION OF PREFERRED EMBODIMENTS

Figure 1:
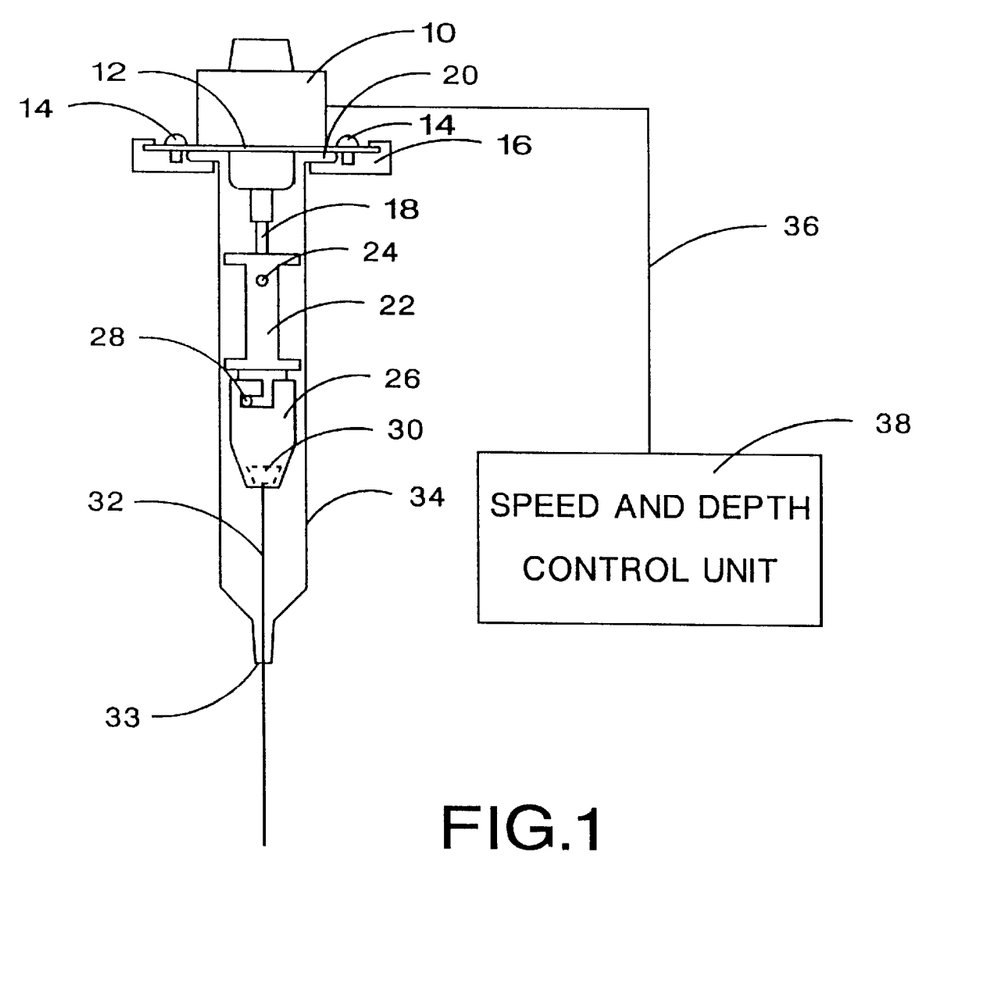
FIG. 1 is a side elevational view showing an embodiment of an automated intramuscular stimulation needling device which does not include the puncturing aid of the present invention.

FIG. 1 shows the principal structures of a motor driven intramuscular stimulation (IMS) needling device, and its connection to a controller for purposes of adjusting the speed and depth of a poking procedure.

To treat a patient, an operator positions a syringe body associated with the needling device above the patient's skin, directly above the involved muscle. The syringe body includes a portal through which a needle can pass, to move in and out freely. The control unit is then activated to cause desired movement of the needle. Once energized, the needle moves back and forth at a frequency set by the control unit, and for a preset length (i.e., the depth of the poking) which is also determined by the control unit. As a result, the needle is caused to penetrate the skin and to begin stimulating the target muscle, which then takes place repeatedly until the needle is withdrawn.

The needling device is generally comprised of six major component parts including a linear motor 10, a syringe holder 16, a syringe body 34, a plunger 22, a needle holding cap 26, and needle 32. The linear motor 10 has internal gears (not shown) that convert the rotational motion of the motor into a linear motion that can be transferred to the shaft 18. Linear motors that can provide such operation are available from Philips Technologies, of Cheshire, Conn. The direction of rotation of the motor determines the direction of the linear movement of the needle 32. For example, when the motor 10 turns clockwise, the shaft 18 moves downwardly, whereas the shaft 18 moves upwardly when the motor 10 turns counterclockwise. The control unit 38 sends the motor 10 both the movement signal and the direction signal by the electrical lines 36.

The syringe holder 16 receives the syringe body 34. To this end, the syringe holder 16 is advantageously implemented as a machined part, fixed to the base plate 12 of the motor 10 by two retaining screws 14, and forming a housing for a base plate 20 associated with the syringe body 34. The syringe holder 16 is preferably made of a material, such as "Plexiglas®", which can be machined so that the syringe body 34 can be easily attached to and detached from the syringe holder 16, for example, by a twist-lock mechanism. The syringe body 34 is further preferably made of a transparent polymer material so that the inner motion of the needle 32 can be seen from outside of the syringe body 34. As an example, a commercially available, 10 cc disposable syringe can be used for the syringe body 34.

The plunger 22 is preferably implemented as a machined part made of a suitable plastic material such as "Lexan®", "Nylon®" or "Teflon®", and has the purpose of linking the motor 10 and the needle 32. As shown in FIG. 1, one side of the plunger 22 is attached to the motor shaft 18 by a set screw 24. The opposite side of the plunger 22 has a retaining pin 28 for retaining a needle holding cap 26, for example, by a twist-lock mechanism.

The needle holding cap 26 is preferably implemented as a machined part, and operates to hold the needle 32 firmly in place so that the needle 32 is aligned along the axis of the shaft 18 during the treatment of a patient. The upper end of the cap 26 has a twist-lock slot, to permit rapid needle replacement. The lower end of the cap 26 has a machined hole to receive the head 30 of the needle 32.

The needle 32 is preferably of a very small diameter (such as an acupuncture needle), for efficient insertion into the skin and muscle tissue. The needle 32 preferably has a plastic head 30 to make the needle 32 more convenient to hold.

The syringe body 34, the needle holding cap 26, and the needle 32 of the needling device should be made replaceable so that these parts can be sterilized each time, before they are used to treat a new patient. To replace a needle 32, the syringe body 34 is first twisted off from the syringe holder housing 16. The holding cap 26 is then twisted off from the plunger body 22, and the needle 32 is finally removed from the holding cap 26. These steps are reversed to mount a new needle 32.

Figure 2:
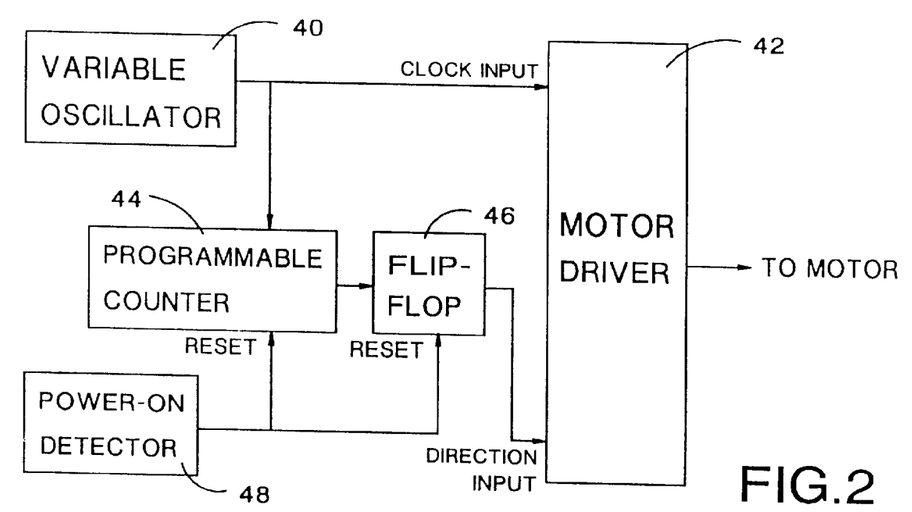
FIG. 2 is a block diagram showing a speed/depth control unit for an automated intramuscular stimulation needling device of the present invention.

The speed and depth control unit 38 is either a battery or an electrically powered electronic unit that operates to control the linear movement of the motor 10 both in terms of its speed and the length of the stroke which is developed. As shown in FIG. 2, the control unit 38 is comprised of five main circuit elements including a variable oscillator 40, a motor driver 42, a programmable counter 44, a flip-flop 46, and a power-on detector 48.

Figure 3:
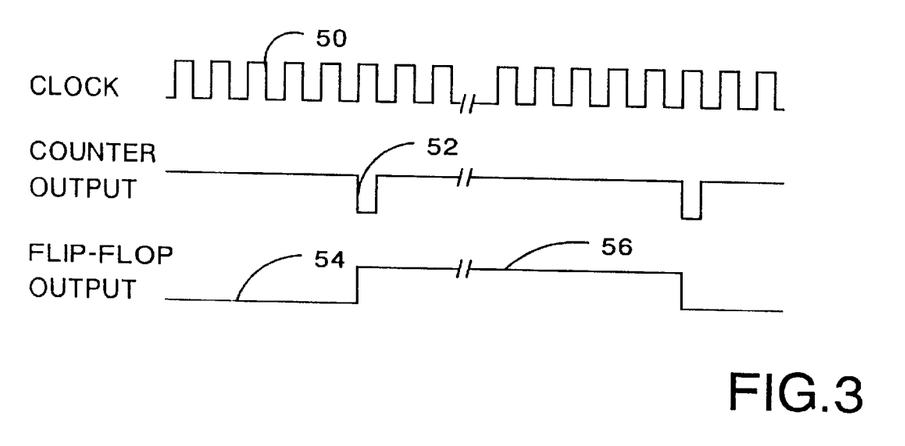
FIG. 3 is a graph showing the timing logic of the control unit of FIG. 2.

The variable oscillator 40 generates a square wave signal, such as that shown at 50 in FIG. 3. The frequency of the clock signal for developing the square wave signal is preferably made adjustable. The variable oscillator 40 can be implemented either using a crystal-based oscillator circuit or a timer integrated circuit chip (e.g., a conventional 555 timer chip).

The motor driver 42 operates to send the necessary power to the motor 10 for linearly moving the shaft 18. To this end, the motor driver 42 requires a clock input and a direction input. The clock input is preferably a pulse train such as is shown at 50 in FIG. 3. Each pulse moves the motor shaft 18 by a fixed distance. Therefore, if one pulse moves the motor shaft by 0.02 inches, then 20 pulses will be required to move the motor shaft by 0.4 inches, and so on. The frequency of the clock pulse determines the speed of movement. For example, if the clock rate generated by the variable oscillator 40 is 100 Hz, the motor shaft 18 will move 2 inches per second when each pulse moves the motor shaft 18 by 0.02 inches. The motor driver 42 also requires a directional input. The directional input is a logic signal that determines the direction of movement of the motor shaft 18. For example, when the logic signal is high, the movement of the motor shaft 18 will be in a forward direction, whereas when the logic signal is low, the movement of the motor shaft 18 will be in the reverse direction.

The programmable counter 44 operates as a source for generating the direction signal for the motor driver 42. The counter 44 has a preset count value, which is decremented by one as each clock pulse is counted by the counter 44. When the terminal count is reached, the programmable counter 44 generates a logic pulse corresponding to one clock pulse, as shown at 52 in FIG. 3. This logic pulse signal is then fed to the flip-flop circuit 46. After the terminal count is reached, the programmable counter 44 re-loads the preset count value and repeats the same operation to generate the next pulse signal. The preset count value is programmed, and is selectable by the operator.

The flip-flop circuit 46 is a logic circuit that changes its output logic level upon accepting an input pulse signal, as is shown schematically in FIG. 3. When there is no pulse signal input from the programmable counter 44, the output of the flip-flop 46 is low, as shown at 54 in FIG. 3. When the flip-flop 46 receives a logic pulse, its output changes logic state, as shown at 56 in FIG. 3. Because the programmable counter 44 generates a clock pulse at the terminal count, the output of the flip-flop 46 changes its logic state at the end of each terminal count. This means that the directional input to the motor driver 42 will change at every terminal count of the programmable counter 44. This, in turn, changes the direction of movement of the motor shaft 18.

The power-on detector 48 generates a logic pulse when the power is turned on. This pulse is then fed to the reset inputs of the programmable counter 44 and the flip-flop 46. Upon receiving this pulse, both the programmable counter 44 and the flip-flop 46 reset their outputs so that the control unit 38 will start its operation at the same logic state every time the power is turned on.

Figure 4:
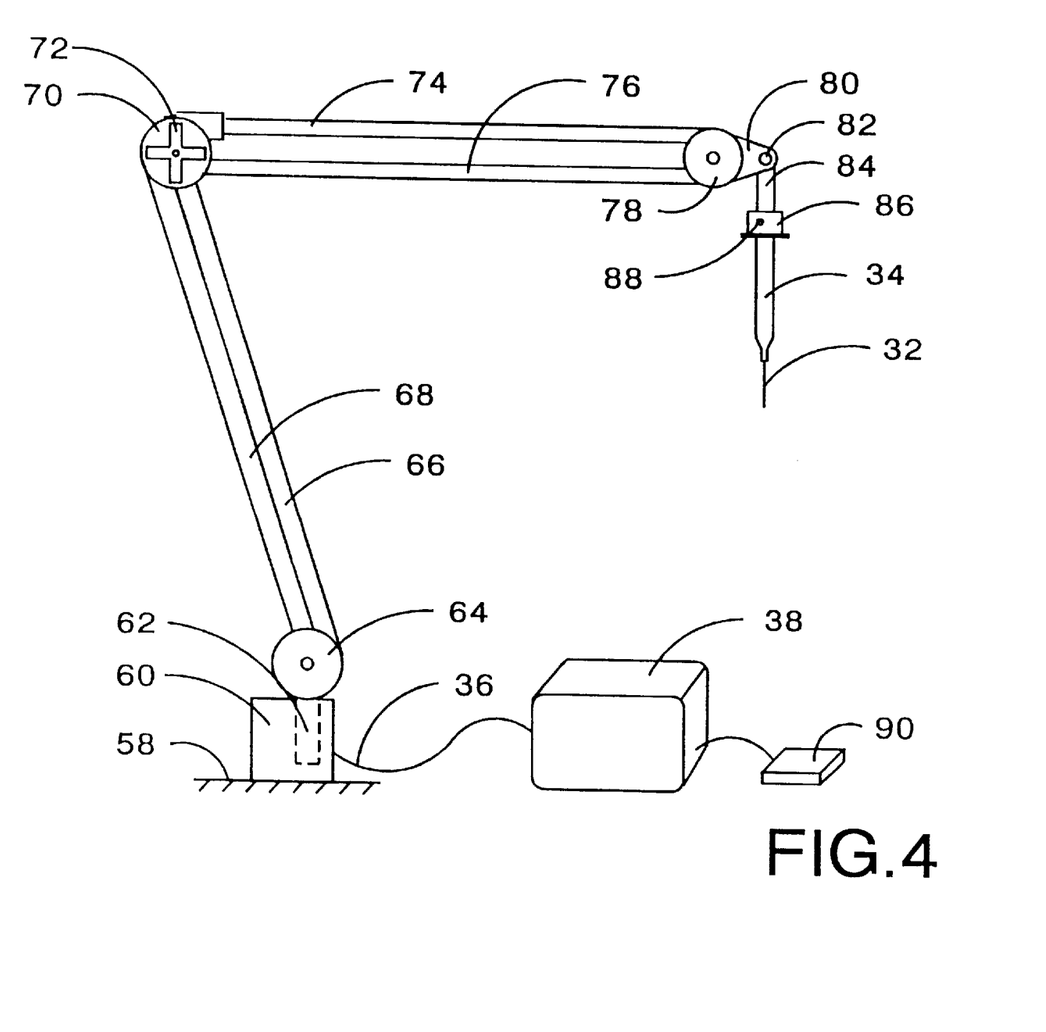
FIG. 4 is a side elevational view showing an overall arrangement for supporting the intramuscular stimulation device in desired position.

To perform an intramuscular stimulation treatment, the needling device can be hand-held by grasping the syringe body 34. However, holding the needling device in a fixed position for an extended period can become burdensome to the operator. Such physical effort can be relieved by using a mechanical swivel arm to hold the needling device while the operator positions the needling device at the desired treatment position. One such arrangement is shown in FIG. 4. In this configuration, the syringe body 34 is held by a mechanical swivel arm comprised of the parts 60 through 82. To this end, the needling device is attached to a tool holder assembly 80 by a motor holder housing 86. The holder housing 86 is preferably implemented as a machined part formed of aluminum. The head of the motor 10 is placed in the holder housing 86 and is fixed in position with a set screw 88. The holder housing 86 has a short handle 84 that is attached to the tool holder assembly 80 using a set screw 82.

The swivel arm allows for positioning of the needling device in all directions within the reach of the arm. To this end, the arm has three joints including a base joint 64, a middle joint 70 and an end joint 78. Two beams extend between the joint 64 and the joint 70, including an upper arm beam 66 and a lower arm beam 68. Two beams also extend between the middle joint 72 and the end joint 78, including an upper forearm beam 74 and a lower forearm beam 76. The joints 64, 70, 78 permit bending and stretching of the arm beams 66, 68 and the arm beams 74, 76. The stiffness of the assembly, in terms of bending and stretching, is adjusted by tightening or loosening an adjustment screw 72. The swivel arm is fixed on a solid surface 58 by a mounting base 60. The base 60 has a recess for accepting a base pin 62. This arrangement allows 360° rotation of the swivel arm. The swivel arm is preferably constructed from a material such as steel.

The arm beam 76 and the arm beam 66 are preferably hollow to carry the electrical wiring from the motor 10. The electrical connection to the control unit 38 is made at the base 60 of the swivel unit, as shown in FIG. 4. A foot switch 90 is preferably connected to the control unit 38 for remotely starting and stopping the motor.

When the intramuscular stimulation needling device is attached to the swivel arm, as shown in FIG. 4, the needle 32 can be moved freely in all directions. To treat a patient, the needle 32 is first moved, by extending the mechanical swivel arm, to a position over the patient's skin under which the muscle to be treated lies. After this positioning, and following initial insertion of the needle 32, the foot switch 90 is pressed to activate the control unit 38. In this way, use of the operator's hand and muscles is minimized, which enables the operator to practice intramuscular stimulation treatments for an extended period of time without the potential for injury.

In practice, it has been found that special attention is appropriately given to the initial insertion of the needle 32 into the patient's skin following the above-mentioned positioning of the mechanical swivel arm. Such considerations will apply equally to treatments using the needling device without the assistance of the swivel arm. The reason for this is that in order to begin an intramuscular stimulation treatment, the needle 32 must initially puncture the skin. However, the skin is often very tough and resistant to puncturing, even with a very sharp needle, especially when an affected muscle is located underneath the skin being punctured. To minimize the potential pain associated with this aspect of the treatment procedure, the initial puncturing step has to be performed as quickly as possible.

Figure 5:
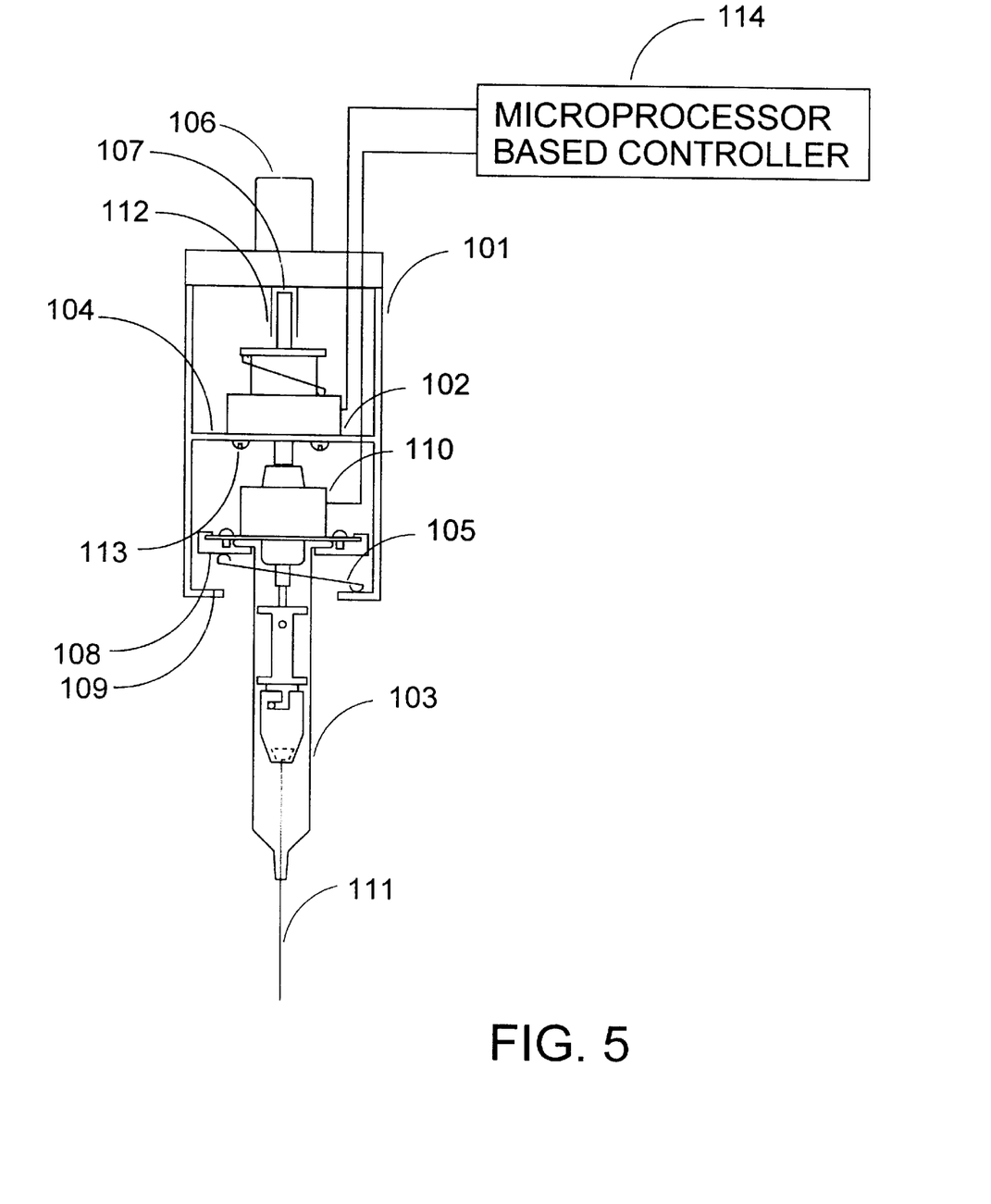
FIG. 5 is a side elevational; view similar to FIG. 1, showing an embodiment of an automated intramuscular stimulation needling device having a puncturing aid produced in accordance with the present invention.

To further minimize the potential for pain during initial insertion of the needle, the alternative embodiment needling device shown in FIG. 5 can be used. The needling device shown in FIG. 5 includes all of the basic elements of the needling device shown in FIG. 1, with the addition of an aid for initially puncturing the skin to reduce the potential for pain during this portion of the intramuscular stimulation treatment.

The puncturing aid is housed within a cylindrical column 101, and includes a solenoid 102 placed in series with the intramuscular stimulator 103 (which corresponds in structure to the needling device shown in FIG. 1). To this end, the solenoid 102 is fixed on a circular plate 104 formed in the top part of the column 101 (e.g., using set screws 113). The intramuscular stimulator 103 is suspended in the lower part of the column 101, and is biased into engagement with the solenoid 102 by a spring 105. The column 101 has a cylindrical handle 106 that can be fixed to a mechanical arm, such as the arm shown in FIG. 4, if desired. A guide 112 is preferably provided for receiving the shaft 107 of the solenoid 102.

To begin puncturing of the skin, the needle 111 is first positioned very close to the skin. The solenoid 102 is then energized, causing the shaft 107 of the solenoid 102 to abruptly be pushed downwardly. This action pushes the entire intramuscular stimulator 103 downwardly, in turn causing the needle 111 to puncture the skin. At this point, the spring 105 is compressed between the mounting plate 108 associated with the motor 110 (which is preferably a stepper-motor) and the bottom 109 of the column 101.

Before the solenoid 102 is deactivated, the motor 110 is preferably turned on to advance the needle 111 further downwardly and into the skin (and the affected muscle) so that when the solenoid 102 is deactivated and the shaft 107 returns to its original position, the needle 111 will be left inside of the skin. From this point forward, normal treatment with the intramuscular stimulator 103 begins, and proceeds as previously described. The solenoid 102 is de-energized when the desired (single) treatment procedure is over.

Figure 6:
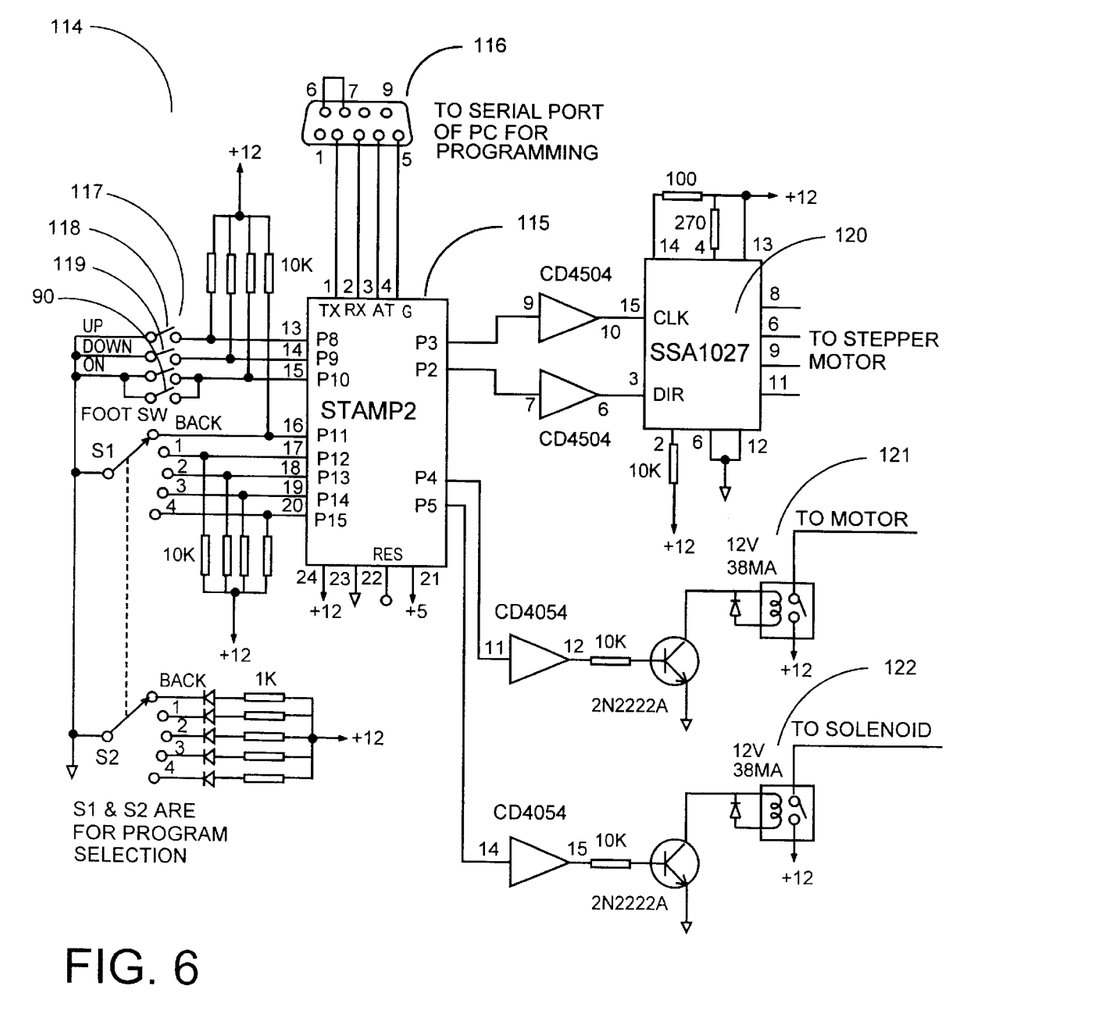
FIG. 6 is a schematic diagram showing a control unit for operating the automated intramuscular stimulation needling device of FIG. 5.

The timing for energizing and de-energizing the solenoid 102 is preferably established by a microprocessor-based controller, such as the controller 114 shown in FIG. 6. The stepper-motor 110 is also controlled by the controller 114. A preferred implementation for such a controller utilizes a STAMP2 microcontroller chip (available from Digi Key, of Minnesota), as is shown in FIG. 6. However, other microcontroller chips can similarly be used to develop a controller 114 having equivalent functions.

In the configuration of FIG. 6, the controller 114 operates responsive to a microprocessor 115, such as the STAMP2 microprocessor previously mentioned. The microprocessor 115 communicates with a computer (such as a PC) for establishing desired programming associated with a desired intramuscular stimulation treatment, preferably by a serial port connection 116. Also in communication with the microprocessor 115 are the various controls for regulating operations of the needling device as previously described. For example, a first grouping of controls 117 includes switches 118, 119 for moving the needling device up and down, and the foot switch 90. A second grouping of controls includes switches S1 and S2, which are provided to allow the operating parameters of the needling device to be regulated (such as the speed and stroke of the needling procedure). The microprocessor 115 is further coupled with a driver circuit 120, which is in turn coupled with the stepper motor 110, and a pair of relay driving circuits including a first driving circuit 121 for energizing the stepper motor 110 and a second driving circuit 122 for energizing the solenoid 102. The circuit elements shown in FIG. 6 operate in known fashion to effectively regulate operations of the stepper motor 110 and the solenoid 102, as previously described, to perform desired intramuscular stimulation treatments.

It is to be understood that while the foregoing description contains many specific references, these references should not be construed as limiting the scope of the invention, but rather should be considered as merely providing illustrations of some of the presently preferred embodiments of this invention. Thus, the scope of the invention should be determined by the appended claims and their legal equivalents, rather than by the examples given above.

What I claim is:

1. In a motor-driven intramuscular stimulation needling device for relieving chronic muscular pain including a needle and an electrically powered motor for inserting the needle into an affected muscle so that said needle produces a repeated, controlled motor-driven back and forth poking of said muscle, an energy source for energizing said motor, and a mechanical linkage linking said needle to said motor for causing a linear back and forth motion to said needle when said motor is energized, the improvement which comprises:

puncturing means associated with said needling device for causing said needle to puncture skin located over said affected muscle; and means for activating said puncturing means so that said needle is automatically caused to puncture said skin.

2. The device of claim 1, wherein said puncturing means is a solenoid.

3. The device of claim 1, wherein said mechanical linkage includes a shaft for receiving said needle and for connection to said motor in a linear relation so that said motor moves said shaft back and forth in a controlled, linear motion for imparting said linear back and forth motion to said needle, wherein a tubular housing receives said needle and said shaft, said tubular housing having one end attached to said motor and a portal at an opposite end for passing said needle freely in and out of said tubular housing, and wherein said device further comprises a cylindrical column which receives said tubular housing so that said needle extends from an opening in said cylindrical column, and a solenoid attached to said cylindrical column and extending between said cylindrical column and said tubular housing.

4. The device of claim 3, further comprising a spring located between said cylindrical column and said tubular housing, for biasing said needling device away from said opening in said cylindrical column.

5. The device of claim 1, further comprising an electrical control unit for electrically controlling said motor, wherein said control unit is further coupled with said activating means.

6. The device of claim 5, wherein said control unit has programmable means for controlling timing of operations of said puncturing means.

7. The device of claim 1, further comprising a mechanical swivel arm for holding said device in a fixed position at a treatment site.

8. The device of claim 7, wherein said swivel arm is movable in all directions.

9. In a motor-driven intramuscular stimulation needling device for relieving chronic muscular pain including a needle and an electrically powered motor for inserting said needle into an affected muscle so that said needle produces a repeated, controlled motor-driven back and forth poking of said muscle, an energy source for energizing said motor, and a mechanical linkage linking said needle to said motor for causing a linear back and forth motion to said needle when said motor is energized, the improvement which comprises:

a solenoid associated with said needling device so that said needle is caused to puncture skin located over said affected muscle.

10. In a method for relieving chronic muscular pain using an intramuscular stimulation treatment including insertion of a needle into an affected muscle and poking said muscle repeatedly with said needle, wherein said method is made less uncomfortable for a patient and less of a strain on a treatment administrator by applying at a treatment site a motor driven needle stimulator device including a needle and an electrically powered motor for driving said needle in a uniform, controlled back and forth linear motion having a fixed distance and frequency, for repeatedly inserting said needle into said muscle, and energizing said motor while holding said stimulator device at said treatment site for a required treatment time interval, the improvement which comprises the steps of:

providing said stimulator device with a puncturing device for causing said needle to puncture skin located over said affected muscle, and activating said puncturing device, automatically causing said needle to puncture said skin located over said affected muscle.

11. The method of claim 10, wherein the puncturing device is a solenoid, and wherein the method further comprises the step of activating said solenoid to cause said needle to puncture said skin.

12. The method of claim 11, further comprising the step of normally biasing said puncturing device in a direction away from said skin.

13. The method of claim 11, further comprising the step of activating the stimulator device before deactivating the solenoid.

14. The method of claim 10, further comprising the steps of providing said motor driven needle stimulator device with an adjustable swivel arm for holding said stimulator device at said treatment site in a fixed position, and grasping said stimulator device with said swivel arm while applying said stimulator device to said treatment site for said required treatment time interval.

15. The method of claim 10, further comprising the step of programming operations of said puncturing device to control timing of operations of said puncturing device.

* * * * *